United States Patent [19]

Dworkin et al.

[11] 4,124,618
[45] Nov. 7, 1978

[54] METHOD FOR PREPARING BIS(ORGANOTIN MERCAPTOALKANOL ESTER) SULFIDES

[75] Inventors: Robert D. Dworkin, Old Bridge; Adam J. Ejk, Piscataway, both of N.J.

[73] Assignee: M&T Chemicals Inc., Stamford, Conn.

[21] Appl. No.: 738,132

[22] Filed: Nov. 2, 1976

[51] Int. Cl.$^2$ ............................ C11C 3/00; C07F 7/22
[52] U.S. Cl. .................................. 260/410.6; 260/399; 260/410; 260/429.7
[58] Field of Search .................... 260/429.7, 399, 410, 260/410.6

[56] References Cited

U.S. PATENT DOCUMENTS

| | | | |
|---|---|---|---|
| 2,832,750 | 4/1958 | Weinberg et al. | 260/429.7 X |
| 2,870,182 | 1/1959 | Leistner et al. | 260/429.7 |
| 2,885,415 | 5/1959 | Ramsden | 260/429.7 |
| 3,565,931 | 2/1971 | Brecker | 260/429.7 |
| 3,931,263 | 1/1976 | Molt | 260/429.7 |
| 3,979,359 | 9/1976 | Kugele et al. | 260/429.7 X |

Primary Examiner—Helen M. S. Sneed
Attorney, Agent, or Firm—Kenneth G. Wheeless; Robert Spector

[57] ABSTRACT

Organotin derivatives of mercaptoalcohol esters that correspond to the general formula

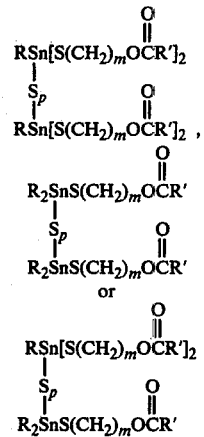

wherein R and R' are hydrocarbon, m is 2 or 3, and p is 1 or 2 are prepared by sequentially reacting a quantity of a monoorganotin trihalide, a diorganotin dihalide or an equimolar mixture of a mono- and a diorganotin halide containing n moles of halogen with n-2 equivalent weights of a base, n-2 moles of a mercaptoalcohol, 0.5 mole of an alkali metal sulfide when p is 1 or an alkali metal disulfide when p is 2, for every mole of tin present and n-2 moles of an carboxylic acid or ester thereof. The present method offers advantages over the prior art, which teaches reacting an esterified mercaptoalcohol with an organotin halide, oxide or organostannoic acid. Compounds wherein R' is n-heptyl are unique in that they do not exhibit the disagreeable odor that characterizes this class of compounds.

12 Claims, No Drawings

METHOD FOR PREPARING BIS(ORGANOTIN MERCAPTOALKANOL ESTER) SULFIDES

BACKGROUND

This invention relates to a method for preparing a particular class of organotin compounds. This invention further relates to a method for preparing organotin derivatives of mercaptoalcohol esters which offers advantages with respect to known methods for preparing this class of organotin compounds.

U.S. Pat. No. 2,870,182 discloses compounds of the general formula $R_nSnA_{4-n}$ wherein R represents one of a specified group of hydrocarbon radicals, n is 1, 2 or 3 and A represents the residue obtained following removal of the hydrogen atom from the —SH group of a mercaptoalcohol ester. The patent further disclosed that compounds corresponding to the foregoing formula can be prepared by first reacting the mercaptoalcohol with a carboxylic acid in the presence of a suitable esterification catalyst and subsequently reacting the resultant ester with an organotin halide, oxide or an organostannoic acid. This preparative method is less than desirable for a number of reasons. Firstly, formation of the mercaptoalcohol ester is an equilibrium reaction which almost always requires an acidic catalyst and removal of water during the reaction to obtain a useful yield of the desired product within a reasonable length of time. The acid catalyst may promote a number of undesirable side reactions, including polymerization of the mercaptoalcohol. The polymer may contain end groups that will subsequently react with the organotin compound, however the reaction product is not nearly as effective as the desired monomeric ester derivative in a number of applications, including stabilization of vinyl chloride polymers. A second undesirable feature of the aforementioned prior art method is that removal of water is required during preparation of the ester and during reaction of the ester with the organotin compound. Removal of water requires heating, which not only increases processing costs due to the additional energy input but can result in larger amounts of undesirable by-products due to side reactions. In addition, a portion of the mercaptoalcohol usually distills together with the water. It has now been found that the disadvantages inherent in the prior art method can be avoided if the mercaptoalcohol is first reacted with the organotin compound and then esterified. Reactions of organotin halides and oxides with both mercaptans and alcohols are reported in the chemical literature. One would therefore expect a mixture of products containing tin-oxygen and tin-sulfur bonds. Surprisingly, under the conditions disclosed hereinafter only the mercaptide (—SH) portion of the mercaptoalcohol reacts with the organotin compound. The hydroxyl portion of the molecule remains available for subsequent esterification with a carboxylic acid.

SUMMARY OF THE INVENTION

This invention provides a method for preparing an organotin compound of the general formula

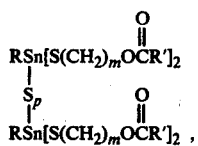

-continued

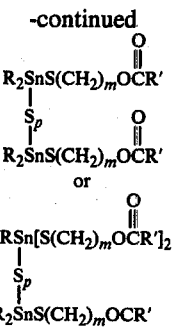

wherein R and R, are individually selected from the group consisting of alkyl containing from 1 to 20 carbon atoms, cycloalkyl, aralkyl, aryl and alkaryl, m is 2 or 3 and p is 1 or 2, said method consisting essentially of the following sequence of steps:

(1) reacting a monoorganotin trihalide of the formula $RSnX_3$, a diorganotin dihalide of the formula $R_2SnX_2$, or an equimolar mixture of $RSnX_3$ and $R_2SnX_2$ wherein X is a halogen selected from the group consisting of chlorine, bromine and iodine, with an aqueous solution containing a base selected from the group consisting of alkali metal hydroxides and alkoxides, alkaline earth metal hydroxides and alkoxides and ammonium hydroxide, wherein the ratio of the number of equivalent weights of base to the number of moles of halogen initially present in the organotin halide is $n-2:n$, respectively;

(2) adding $n-2$ moles of 2-mercaptoethanol or 3-mercaptopropanol to the resultant mixture;

(3) adding to the reaction product of step 2 an alkali metal sulfide, when p is 1 or an alkali metal disulfide when p is 2, the number of moles of sulfide or disulfide being equal to 0.5 times the number of moles of tin present in said reaction product;

(4) reacting the product obtained thereby with $n-2$ moles of carboxylic acid, R'COOH, or an ester R'COOR" wherein R" is alkyl and contains from 1 to 20 carbon atoms;

(5) removing any by-product water from the resultant mixture to isolate said organotin compound.

DETAILED DESCRIPTION OF THE INVENTION

The first step of the present method for preparing mono- and diorganotin derivatives of mercaptoalcohol esters comprises reacting the corresponding organotin halide of the formula $RSnX_3$, $R_2SnX_2$ or an equimolar mixture of a mono- and a diorganotin halide with an aqueous solution of a base. The quantity of base employed is sufficient to react with all but one of the halogen atoms present on each organotin halide molecule. It will be understood that two equivalent weights of base are required for each mole of a monoorganotin trihalide while one equivalent weight is employed for each mole of a diorganotin dihalide. All of the base can be added initially to react with the organotin halide. Alternatively, a major portion of base, usually about 90% of the total, is added initially and the remainder is added following addition of the alkali metal sulfide.

As disclosed in the preceding specification, the term X in the foregoing formulae represents chlorine, bromine or iodine and R represents an alkyl group containing from 1 to 20 carbon atoms, a cycloalkyl, aryl, alkaryl or an aralkyl group. When R is alkyl it can be methyl, ethyl, n-propyl, iso-propyl or any higher homolog containing up to 20 carbon atoms. Suitable cycloalkyl radicals include, for example, cyclopropyl, cyclobutyl, cyclohexyl and cyclooctyl. When R is aryl it is preferably phenyl but R may also represent naphthyl, anthrecenyl or biphenyl. Suitable aralkyl radicals include, for example, benzyl and Δ-phenylethyl. When R is alkaryl it can be, for example one of the isomeric tolyl, xylyl or other alkyl-substituted phenyl radicals.

The base employed is ammonium hydroxide, an alkali metal hydroxide, such as sodium hydroxide, or an alkaline earth metal hydroxide, for example calcium hydroxide. A corresponding alkoxide, such as sodium methoxide, can be employed in the place of any hydroxide.

The reaction between the halogen atoms of the organotin halide and the base is rapid at ambient temperature and often highly exothermic. The addition of the organotin halide should therefore be gradual and the reaction mixture is simultaneously stirred and cooled to prevent localized overheating. It may be desirable to continue stirring the reaction mixture after all of the organotin halide has been added in order to improve heat transfer and increase the rate of cooling. The resultant solution of an organotin hydroxyhalide is then reacted with the desired mercaptoalcohol. The rate of this reaction is considerably slower than the rate at which the initial organotin halide reacts with a base. It may therefore be desirable to maintain the mixture at a temperature from 40° to 100° C. to complete the reaction in a reasonable length of time, usually from 5 to 60 minutes. The number of moles of mercaptoalcohol added is equal to the number of equivalent weights of base employed in the initial step of this method.

The most readily available mercaptoalcohols are 2-mercaptoethanol and 3-mercaptopropanol. These compounds are therefore preferred for use in the present method. Other known mercaptoalcohols, for example 4-mercapto-1-butanol, would be equally suitable.

When the reaction of the organotin compound with the mercaptoalcohol is completed, the resultant mixture is combined with one mole of an alkali metal sulfide for every two moles of tin present in the reaction mixture when $p$ of the foregoing formula is 1. When $p$ is 2, an alkali metal disulfide is employed. The disulfide can be formed by reacting equimolar amounts of alkali metal sulfide and elemental sulfur. Preferably the sulfide or disulfide is added to the organotin component gradually, since the reaction may be exothermic. The sulfide or disulfide can be added as a solid or in an aqueous solution. Any base not added during the initial hydrolysis of the halide is added at this time.

Following the completion of the sulfide addition the mercaptoalcohol residue is esterified by addition of the desired carboxylic acid, R'COOH, or an ester thereof, R'COOR", derived from an alcohol containing from 1 to 20 carbon atoms. Suitable acids contain from 2 to 20 carbon atoms and the hydrocarbon residue is alkyl, cycloalkyl, aryl, aralkyl or alkaryl as previously disclosed for the hydrocarbon portion of the organotin halide reactant. R' may contain one or more substituents such as halogen, hydroxyl, alkoxy and nitro (NO$_2$) groups. In contrast to conventional esterification reactions, a stoichiometric excess of carboxylic acid is not required, nor is it necessary to add a catalyst. Octanoic acid, also known as caprylic acid, is preferred in that products prepared using this acid do not exhibit the disagreeable odor which characterizes this class of organotin compounds. If an ester of the acid is employed, the alcohol residue preferably contains from 1 to 4 carbons to facilitate removal of the alcohol by distillation during the transesterification reaction. In those instances when the final organotin compound will be used as a stabilizer for halogenated polymer such as polyvinyl chloride it may be desirable to employ a higher moleculsr weight alcohol containing from 12 to 20 carbon atoms as the alcohol component of the aforementioned ester R'COOR". In this instance the alcohol R"OH would not be removed during the transesterification, but rather is isolated together with the final organotin product. The alcohol serves as a lubricant or processing acid in the stabilized halogenated polymer composition.

Once the acid or ester has been added the aqueous phase of the reaction mixture is removed and discarded. Following removal of the aqueous phase, the reaction mixture is heated to 100°–180° C. to effect the esterification or transesterification reaction. If the by-product is water or a volatile alcohol boiling below about 120° C., the by-product is continuously removed during the reaction using a suitable distillation apparatus. To minimize overheating and the accompanying product decomposition the final portion of water is preferably removed under a reduced pressure that is usually equivalent to 10–100 mm. of mercury. Once all of the water or alcohol has been removed the final liquid organotin compound remains in the reaction vessel. It may be necessary to filter the product to remove small amounts of solid materials.

The products obtained using the present method are useful for the same applications as other mono- and diorganotin compounds containing tin-sulfur bonds. The present compounds are particularly effective heat stabilizers for vinyl chloride polymers and other high molecular weight halogen-containing polymers. The compounds are conventionally employed for this purpose at concentrations of from 0.1 to 10% by weight. Organotin derivatives of mercaptoalcohol esters may also find use as antioxidants for a variety of materials. The following examples demonstrate preferred embodiments of the present method and, as such, should not be interpreted as limiting the scope of the accompanying claims.

EXAMPLE 1 - Preparation of bis(monobutyltin di-2-mercaptoethyl pelargonate) sulfide A reaction vessel was charged with 20.88 g. (0.36 mole) of aqueous ammonium hydroxide and 50 cc. of water. To this mixture was gradually added 56.44 g. (0.20 mole) of monobutyltin trichloride. The contents of the reaction vessel were stirred during the addition and for one-half hour thereafter, at which time 31.92 g. (0.40 mole) of 2-mercapto-ethanol (98% purity) was added in a single portion to the reaction mixture. The contents of the reaction vessel were then heated to 60° C. and maintained at that temperature for 15 minutes. When the mixture had cooled to 40° C. a 13.0 g. (0.10 mole) portion of solid sodium sulfide was added over a period of about thirty minutes. The contents of the vessel remained undisturbed for 10 minutes following completion of the addition, at which time the pH of the mixture was adjusted to 6.5 using 0.04 mole of ammonium hydroxide and the mixture heated to a temperature of 55° C. To the heated mixture were added 63.3 g. (0.4 mole) of pelargonic acid. Following addition of the acid the reaction mixture was heated to 85° C. for 20 minutes, at which time the aqueous phase of the two-phase liquid was removed and discarded. The organic layer was returned to the reaction vessel, which was equipped with a distillation apparatus, and heated to 145° C. for 45 minutes. A quantity of water collected in the distillation receiver. The temperature of the mixture in the reaction vessel was then increased to 150° C. and the pressure in the vessel reduced to about 20 mm. of mercury. The liquid remaining in the reaction vessel following completion of the distillation weighed 115 g., corresponding to a yield of 91.7%, based on weight of monobutyltin trihalide.

EXAMPLE 2 - Preparation of Bis[monobutyltin-di(2-mercaptoethyl n-octoate]sulfide A glass reactor equipped with a water cooled reflux condenser, mechanically driven agitator and a thermometer was charged with 56.4 g. (0.2 mole) of monobutyltin trichloride and 50 cc. of water. When the resultant exothermic reaction was complete and the temperature of the mixture had cooled to 40° C., 20.9 g. (0.36 mole) of ammonium hydroxide was gradually added over a period of ½ hour. Forty five minutes following completion of the addition 31.9 g. (0.4 mole) of 2-mercapto-ethanol was charged as a single portion and the contents of the reactor were heated to 70° C. for twenty minutes. When the mixture had cooled to 50° C. a 13.0 g. (0.10 mole) portion of sodium sulfide in flake form was added to the reaction mixture over a period of 25 minutes. Stirring was continued for a ½ hour following completion of the addition, at which time the pH of the mixture was adjusted to 6.5 using 0.04 mole of ammonium hydroxide solution. A 57.7 g. (0.04 mole) portion of n-octanoic acid was then added and the mixture heated to 85° C., at which time the aqueous phase of the reaction mixture was removed and discarded. The reactor was equipped with a distillation apparatus, purged with nitrogen and the contents heated for 2 hours at a temperature of 140° C. A total of 19.4 g. of distillate was collected. The liquid residue in the reactor was isolated by filtration and weighed 103.3 g., which is equivalent to a yield of 86%.

Bis(dibutyltin-2-mercaptoethyl-n-octoate) sulfide can be prepared following the procedure described in the first paragraph of this example, using dibutyltin dichloride in place of butyltin trichloride and adjusting the stoichiometry accordingly (one mole of 2-mercaptoethyl n-octanoate for each mole of dibutyltin dichloride).

[Dibutyltin-2-mercaptoethyl-n-octoate monobutyltin-bis(mercaptoethyl-n-octoate)]sulfide can be prepared using the foregoing procedure, replacing one-half of the molar amount of butyltin trichloride with dibutyltin dichloride and using three moles of base, mercaptoethanol and n-octanoic acid for every two moles of tin present in the reaction mixture.

None of the foregoing compounds exhibit the offensive odor characteristic of monoorganotin or diorganotin derivatives of mercaptoethanol esters. An unpleasant odor is present for analagous compounds wherein the aforementioned n-octanoic acid ester is replaced by the oleic ester of 2-mercaptoethanol. This difference in ordor is also true for the corresponding methyltin derivatives. These compounds are prepared by reacting methyltin trichloride or dimethyltin dichloride in place of the corresponding butyltin chloride.

Bis(monobutyltin-di-2-mercaptoethyl-n-octoate) disulfide can be prepared by dissolving 3.2 g. (0.1 mole) sodium sulfide and 40 cc. water. When the sulfur dissolves 23.6 g. of ammonium hydroxide are added. The resultant solution is employed in place of sodium sulfide in the procedure described in the first paragraph of the preceding Example 2.

What is claimed is:

1. A method for preparing an organotin compound of the general formula

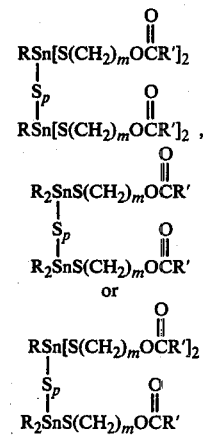

wherein R and R' are individually selected from the group consisting of alkyl containing from 1 to 20 carbon atoms, cycloalkyl, aralkyl, aryl and alkaryl, $m$ is 2 or 3 and $p$ is 1 or 2, said method consisting essentially of the following sequence of steps:
(1) reacting a monoorganotin trihalide of the formula $RSnX_3$, a diorganotin dihalide of the formula $R_2SnX_2$ or an equimolar mixture of $RSnX_3$ and $R_2SnX_2$ wherein X is a halogen selected from the group consisting of chlorine, bromine and iodine, with an aqueous solution containing a base selected from the group consisting of ammonium hydroxide, alkali metal hydroxides and alkali metal alkoxides, wherein the ratio of the number of equivalent weights of base to the number of moles of halogen initially present on the organotin halide is $n$-2:$n$, respectively, and the rate at which the reagents are combined is adjusted to avoid excessive overheating of the reaction mixture;
(2) adding $n$-2 moles of 2-mercaptoethanol or 3-mercaptopropanol to the resultant mixture;
(3) gradually adding to the reaction product of step 2 an alkali metal sulfide when $p$ is 1 or an alkali metal disulfide when $p$ is 2, the number of moles of sulfide or disulfide being equal to 0.5 times the number of moles of tin present in said reaction product;
(4) reacting the product obtained thereby with $n$-2 moles of a carboxylic acid, R'COOH, or an ester R'COOR" wherein R" is alkyl and contains from 1 to 20 carbon atoms;
(5) removing any by-product water from the resultant mixture to isolate said organotin compound.

2. A method as set forth in claim 1 wherein R and R' are individually selected from the group consisting of alkyl radicals containing from 1 to 20 carbon atoms.

3. A method as set forth in claim 2 wherein R is butyl.

4. A method as set forth in claim 1 wherein said carboxylic acid is caprylic acid or pelargonic acid.

5. A method as set forth in claim 1 wherein $m$ is 2.

6. A method as set forth in claim 1 wherein $p$ is 1.

7. A method as set forth in claim 1 wherein X is chlorine.

8. A method as set forth in claim 1 wherein the base reacted with the organotin halide is ammonium hydroxide.

9. A method as set forth in claim 1 wherein the alkali metal sulfide is sodium sulfide.

10. A method as set forth in claim 1 wherein R" contains from 1 to 4 carbon atoms.

11. A method as set forth in claim 1 wherein the alkali metal disulfide is formed by reacting equimolar amounts of said alkali metal sulfide and elemental sulfur.

12. A method as set forth in claim 1 wherein the product of step 3 is reacted with a carboxylic acid ester R'COOR" and the alcohol R"OH formed as a by-product of the reaction is removed by distillation prior to isolating said organotin compound.

* * * * *